United States Patent
Heath et al.

[11] Patent Number: 5,624,259
[45] Date of Patent: Apr. 29, 1997

[54] DENTAL HAND INSTRUMENT

[75] Inventors: Derek E. Heath; Jerry A. Mooneyhan, both of Johnson City, Tenn.

[73] Assignee: Tulsa Dental Products, L.L.C., Tulsa, Okla.

[21] Appl. No.: 435,041

[22] Filed: May 8, 1995

[51] Int. Cl.$^6$ ................................................. A61C 19/04
[52] U.S. Cl. ........................................ 433/72; 433/141
[58] Field of Search ............................ 433/72, 102, 141, 433/142, 143, 144

[56] References Cited

U.S. PATENT DOCUMENTS

| | | | |
|---|---|---|---|
| 1,369,582 | 2/1921 | Wagner | 433/142 |
| 4,197,643 | 4/1980 | Burstone et al. | 433/20 |
| 4,643,676 | 2/1987 | Jansheski | 433/143 |
| 4,643,677 | 2/1987 | Kim | 433/142 |
| 4,743,198 | 5/1988 | Kennedy | 433/143 |
| 5,125,838 | 6/1992 | Seigneurin | 433/102 |
| 5,127,833 | 7/1992 | Kline | 433/141 |
| 5,193,999 | 3/1993 | Staubli | 433/72 |
| 5,244,390 | 9/1993 | Lazzara et al. | 433/143 |
| 5,380,200 | 1/1995 | Heath et al. | 433/102 |

FOREIGN PATENT DOCUMENTS

| | | |
|---|---|---|
| 3620527 | 6/1986 | Germany . |

OTHER PUBLICATIONS

Patent Abstracts of Japan, Publication No. JP4212343; Publication Date: Mar. 8, 1992.

*Wire Journal International, Superelasticity*, "Superelastic Ni–Ti Wire", by Dieter Stoeckel and Weikang Yu, Mar. 1991, pp. 45–50.

*Journal of Endodontics*, "An Initial Investigation of the Bending and Torsional Properties of Nitinol Root Canal Files", by Harmeet Walia et al, vol. 14, No. 7, Jul. 1988, pp. 346–351.

*Primary Examiner*—Cary E. O'Connor
*Attorney, Agent, or Firm*—Bell, Seltzer, Park & Gibson, P.A.

[57] ABSTRACT

A dental hand instrument, such as an explorer, which comprises an elongate rigid handle, and an elongate highly flexible blade attached to one or both ends of the handle. The blade is curved and/or bent along its length and is composed of nickel-titanium alloy, which provides a high degree of flexibility and wear resistance. The high degree of flexibility has been found to significantly enhance the tactile feedback to the hand of the dentist, so that the dentist is able to recognize and distinguish surface cracks, areas of decay, and the like as the point is moved across the exterior surface of a tooth.

6 Claims, 1 Drawing Sheet

DENTAL HAND INSTRUMENT

BACKGROUND OF THE INVENTION

The present invention relates to a hand held dental instrument of the type comprising a handle which is sized for being readily engageable by the dentist, and an elongate blade connected to and extending outwardly from one or both ends the handle.

Instruments of the above type are employed in a number of conventional dental procedures. For example, one instrument of this type, which is commonly referred to as an explorer, comprises a handle and an elongate flexible blade which is composed of stainless steel and which tapers to a sharp point. The dentist holds the instrument in the manner of a pencil and manipulates the point of the blade along the surface of a tooth to check for defects in the enamel caused by cracks, areas of decay, or the like. As will be apparent, a very sharp point is required, since a high degree of sharpness is necessary to provide a "feel" or tactile feedback which the dentist is able to sense and recognize upon encountering a crack or other defect, and to thereby permit an accurate diagnosis of the condition of the tooth. However, conventional stainless steel blades are relatively stiff, which renders the tactile feedback somewhat insensitive, and the point of the stainless steel blade wears relatively quickly, resulting in the need for repeated resharpening operations.

Another dental hand instrument of the described type is referred to as a scaler, which has an arcuate blade of semi-circular or triangular cross-section, and so as to form one or more cutting edges extending along the length direction of the blade. The arcuate configuration of the blade permits it to hug and conform to the exterior surface of a tooth, and when the blade is scraped along the exterior surface of the tooth, it causes removal of tartar and other scale. Here again however, the relative stiffness of the stainless steel from which the blades are made renders the conformance of the blade to the outline of the tooth to be limited, and thus a number of scalers having a variety of configurations are required for each cleaning operation. Also, the stainless steel tends to rapidly wear, causing the cutting edges to be dulled.

Still another dental hand instrument of the described type is referred to as a plugger, which is used during an endodontic root canal procedure to obturate or fill a root canal with gutta percha. In one traditional method of obturating a root canal, strand-like pieces of gutta percha, commonly referred to as "points", are inserted into the previously cleaned root canal. The points are then physically compacted by a plugger, which is inserted into the canal and into contact with the points to compact the points into the canal. Where the apical end of the root canal is severely curved, the plugger is required to flex to a significant degree in order to be able to compact the gutta percha into the apical end. To cause the stainless steel blade to flex to the required degree, it is necessary to impart a significant force to the instrument, and such force in turn causes the instrument to engage and form ledges along the inside wall of the canal. Even more significant however, is the risk that the required axial force may fracture the tooth, which usually requires its subsequent extraction.

A spreader is another dental hand instrument used to obturate root canals, and which is generally similar to a plugger, but which differs from a plugger in that a plugger has a blunt end on the blade whereas a spreader has a pointed end. The spreader thus serves to enter the gutta percha point and compact more in a radial direction, whereas a plugger abuts the upper end of the gutta percha and compacts more in the axial or downward direction. As will be apparent, a spreader also has the danger of ledging the inside wall of the root canal and fracturing the tooth as a result of the required axial force needed to cause it to flex in a curved root canal.

It is accordingly an object of the present invention to provide a dental hand instrument of the described type and which overcomes or at least substantially alleviates the above noted limitations and disadvantages of the known instruments of this type.

It is a more particular object of the present invention to provide a dental explorer which provides significantly more sensitive tactile feedback to the dentist, to thereby permit a more reliable diagnosis of the condition of a tooth.

It is a further object of the present invention to provide a dental scaler which more closely conforms to the exterior surface of a tooth during a cleaning operation, and which is more resistant to wear and dulling of the cutting edges.

It is still another object of the present invention to provide a spreader or plugger for obturating a root canal and which is able to laterally flex under minimal force, so as to permit the instrument to conform to a severely curved root canal without risk of fracturing the tooth.

SUMMARY OF THE INVENTION

The above and other objects and advantages of the present invention are achieved by the provision of a dental hand instrument which comprises an elongate rigid handle which is sized for being readily engageable by the hand of the dentist, and an elongate highly flexible blade connected to and extending outwardly from the handle and terminating in a distal end. The blade is composed of an alloy of nickel and titanium, which preferably comprises at least about 40% titanium and at least about 50% nickel.

In the embodiment where the instrument is particularly adapted for exploring the surface of the tooth to check for defects in the enamel caused by cracks, areas of decay, and the like, the blade has a circular cross sectional configuration which is smooth and non-interrupted, and the distal end portion of the blade is tapered to form a sharp point. Also, the blade is curved and/or bent so that the distal end portion of the blade extends at an angle of at least about 45° with respect to the lengthwise direction of the handle.

BRIEF DESCRIPTION OF THE DRAWINGS

Some of the objects and advantages of the present invention having been stated, others will appear as the description proceeds, when taken in conjunction with the accompanying drawings, in which.

DETAILED DESCRIPTION OF THE PREFERRED EMBODIMENTS

Figure 1:
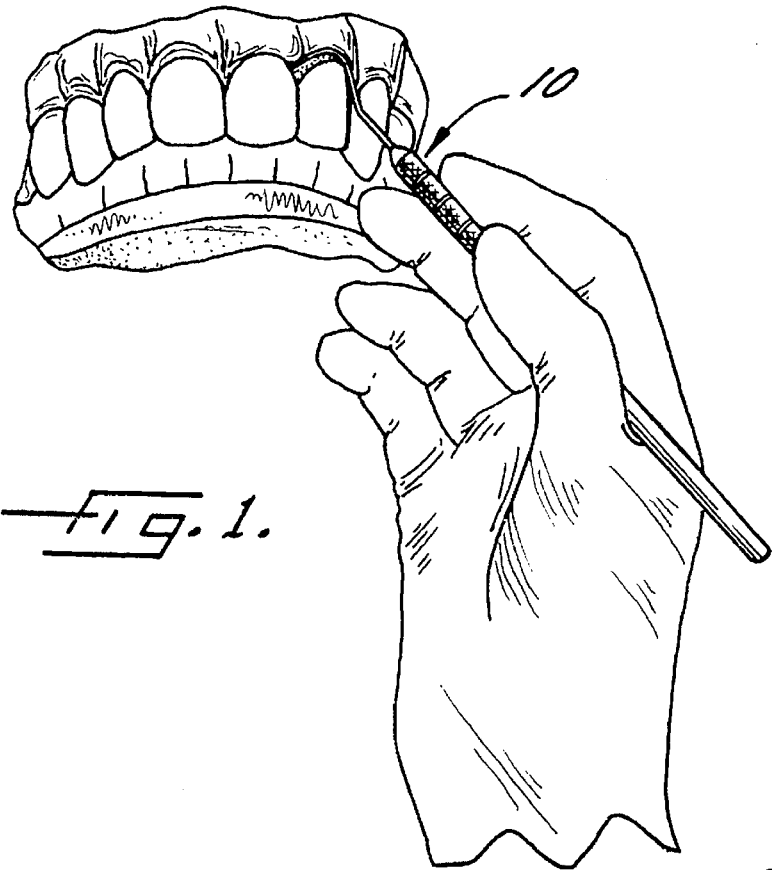
FIG. 1 is a fragmentary perspective view illustrating a dental hand instrument in accordance with the present invention.
Figure 2:
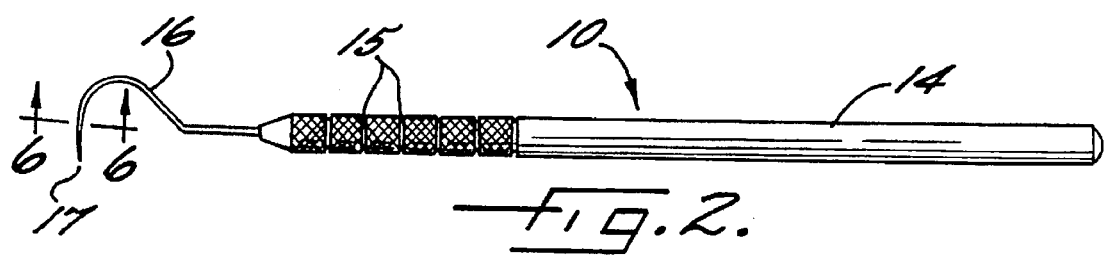
FIG. 2 is a side elevation view of the dental hand instrument illustrated in FIG. 1.

Referring more particularly to the drawings, FIGS. 1 and 2 illustrate dental hand tools 10 and 12, which are in the form of dental explorers and which embody the present invention. The tool 10 comprises an elongate, rigid, and rod-like handle 14 having a length of at least about 2 inches, and typically about 5–6 inches, and a diameter of about ¼ inch. The handle 14 may be fabricated from a suitable metallic material, such as stainless steel, or plastic, and one end of the handle includes a plurality of spaced apart grooves 15 and a knurled surface, to facilitate the non-slip gripping thereof by the hand of the dentist.

Figure 4:
FIG. 4 is a fragmentary view of the point of the instrument shown in FIG. 2.

An elongate blade 16 is connected to and extends outwardly from the knurled end of the handle, and terminates in a distal end 17. The blade has a circular cross-sectional configuration and has a smooth, non-interrupted exterior surface. Also, the blade is about 2 inches in total length and it has a diameter of between about 1 and 2 mm at the end which is connected to the handle. In the embodiment of FIG. 2, the blade 16 includes a linear inner end portion adjacent and coaxial with the handle 14, a bend of about 45 degrees at a medial location along its length, and an arcuate outer end portion, resulting in the distal end portion of the blade which is immediately adjacent the distal end 17 extending at an angle of about 90° with respect to the lengthwise direction of the handle 14. The distal end portion of the blade is tapered at an included angle of between about ½ degree to 5 degrees, and so as to form a sharp point at the distal end 17 as seen in FIG. 4.

In accordance with the present invention, the blade 16 is fabricated from a nickel-titanium alloy which serves to provide a high degree of flexibility and wear resistance. Preferably, the alloy comprises at least about 40% titanium and at least about 50% nickel. In one preferred specific embodiment, the alloy consists of 44% titanium and 56% nickel, and no appreciable amount of other ingredients are present which could adversely effect the purity required for dental instruments.

In use, the dental explorer 10 as described above is held in the hand of the dentist in the manner of a pencil as illustrated in FIG. 1, and the point at the distal end 17 is moved across the surface of the tooth to detect cracks in the enamel and areas of decay. If a crack is present, the sharp point of the instrument enters the crack, which generates a tactile feedback which the dentist is able to sense and recognize. Also, if decay is present, the point penetrates slightly into the relatively compressible decay, and a unique tugback is exerted on the point of the instrument, which usually the dentist can recognize and distinguish from a non-decayed crack.

Surprisingly, the novel alloy composition of the blade 16 of the present invention has been found to provide a greatly enhanced tactile feedback to the dentist. In particular, the nickel-titanium alloy of the present invention provides a high degree of flexibility, which is able to respond to non-uniform surface conditions on the exterior of the tooth to a much greater degree than is a conventional stainless steel blade. Also, the nickel-titanium alloy has been found to provide superior wear resistance at the point, so that the point is able to function properly for extended periods of time, without requiring repeated resharpening operations. Thus the blade 16 of the present invention provides not only an enhanced performance, but also a longer useful life as compared to the presently employed blades of stainless steel.

Figure 3:
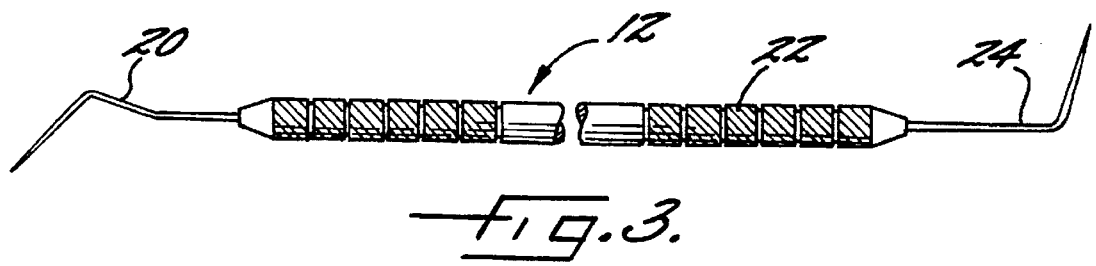
FIG. 3 is a side elevation view of a second embodiment of a dental hand instrument which embodies the features of the present invention.
Figure 6:
FIG. 6 is an enlarged cross-sectional view taken substantially along the line 6—6 of FIG. 2.

FIG. 3 illustrates a second embodiment of the dental explorer of the present invention at 12. In this embodiment, a blade 20 is attached to one end of the handle 22, and a second blade 24 is attached to the other end of the handle, with the two blades 20 and 24 having slightly different outlines. In particular, the blade 20 at the left end as illustrated includes a inner relatively shallow (e.g., 10 degrees) bend and an outer relatively sharp (e.g., 75 degrees) bend, whereas the blade 24 at the right end includes only a single relatively sharp bend at a medial location along its length. The distal end portion of the blade 20 will thus be seen to extend at an angle of about 45 degrees with respect to the lengthwise direction of the handle 22, and the distal end portion of the blade 24 extends at an angle of about 75 degrees. As will be apparent, a variety of similar blade configurations may be provided which are within the scope of the present invention.

Figure 5:
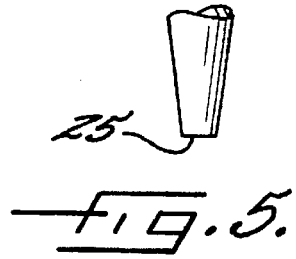
FIG. 5 is a side elevation view of modified point of the instrument shown in FIG. 2 and as typically provided on a plugger as described above.

The present invention is also applicable to dental hand instruments designed for uses other than exploring the surface of a tooth. As noted above, spreaders and pluggers are used in the obturation of a root canal, with the spreader having a sharp point on the blade as illustrated in FIG. 4, and with the plugger having a blunt transverse end surface as seen in FIG. 5 at 25. Spreaders and pluggers typically have a blade configuration similar to that of the blade 20 as seen in FIG. 3. The high degree of flexibility provided by the nickel-titanium alloy of the present invention has been found to substantially alleviate the ledging of the inside wall of the canal, and to also substantially reduce the force required to bend the instrument along a curved canal and compress the gutta percha into the canal, particularly in the case of severely curved canals. This, in turn, substantially reduces the risk that the tooth may be cracked by the force imparted by the instrument during the compaction of the gutta percha.

Figure 7:
FIG. 7 is an enlarged cross-sectional view of the blade of a further embodiment or scaler as described above.
Figure 8:
FIG. 8 is a cross-sectional view of another embodiment of a scaler in accordance with the present invention.

FIGS. 7 and 8 illustrate two possible cross-sectional configurations for blades of a dental scaler which embodies the present invention at 27 and 28. The blade of a scaler typically has an arcuate configuration similar to that shown in FIG. 2, and in the embodiment of FIG. 7, the blade 27 has a semicircular cross-sectional configuration, so as to define two sharp corners or edges which extend along the length of the blade. In FIG. 8, the blade 28 has a triangular cross-section configuration which defines three sharp corners or edges which extend along the length of the blade. Here again, the flexibility of the nickel-titanium blade has been found to permit the blade to closely conform to the outline of the tooth being cleaned, and to thereby provide for an enhanced removal of tartar and the like from the surface of the tooth. Also, the inherent resistance to wear of the nickel-titanium blade avoids the need for repeated sharpening of the cutting edges.

In the drawings and specifications, there has been set forth a preferred embodiment of the invention, and although specific terms are employed, they are used in a generic and descriptive sense only and not for purposes of limitation.

What is claimed is:

1. A dental hand instrument comprising:

an elongate rod-like rigid handle having a length of at least about two inches and sized for being readily engageable by the hand of a dentist, and an elongate highly flexible blade connected to and extending outwardly from the handle and terminating in a sharp point at a distal end, with said blade being non-linear along its length, and with said blade comprising an alloy comprising at least about 40% titanium and at least about 50% nickel.

2. The dental hand instrument as defined in claim 1 wherein said blade includes a distal end portion adjacent said distal end, and at least the distal end portion of said blade is tapered toward said distal end at an included angle of between about ½ degrees and about 5 degrees.

3. The dental hand instrument as defined in claim 2 wherein said blade has a circular cross-sectional configuration along its length and an exterior surface, and wherein the exterior surface of the blade is smooth and non-interrupted.

4. The dental hand instrument as defined in claim 1 wherein said blade has a cross-sectional configuration which defines at least two sharp edges which extend along its longitudinal length.

5. A dental hand instrument which is particularly adapted for exploring the surface of a tooth to check for defects in the enamel caused by cracks, areas of decay, or the like, and comprising an elongate rod-like rigid handle which is sized and configured for being readily engageable by the hand of a dentist in the manner of a pencil, an elongate highly flexible blade connected to and extending outwardly from the handle and terminating in a distal end, said blade having a circular cross sectional configuration along its length and an exterior surface which is smooth and non-interrupted, with the distal end portion of the blade being tapered to form a sharp point, and with the blade comprising an alloy comprising at least about 40% titanium and at least about 50% nickel.

6. The dental hand instrument as defined in claim 5 wherein said handle defines a lengthwise direction, and wherein the blade is non-linear so that the distal end portion of the blade extends at an angle of at least about 45° with respect to the lengthwise direction.

* * * * *